United States Patent [19]

Beigler et al.

[11] 4,282,863

[45] Aug. 11, 1981

[54] METHODS OF PREPARING AND USING INTRAVENOUS NUTRIENT COMPOSITIONS

[76] Inventors: Myron A. Beigler, Two Palo Alto Sq., Palo Alto, Calif. 94304; Amin J. Khoury, 29 Tubwreck Dr., Dover, Mass. 02030

[21] Appl. No.: 926,399

[22] Filed: Jul. 20, 1978

[51] Int. Cl.³ .................... A61B 19/00; A61M 5/00; A61J 1/00
[52] U.S. Cl. ............................ 128/1 R; 128/214 D; 128/272; 206/219
[58] Field of Search ............... 128/214 D, 214 R, 272, 128/1 R; 250/432; 206/219; 131/142; 422/38, 22, 903

[56] References Cited

U.S. PATENT DOCUMENTS

| | | | |
|---|---|---|---|
| 3,494,723 | 2/1970 | Gray | 131/121 |
| 3,648,697 | 3/1972 | Gardner | 128/214 D |
| 3,740,557 | 6/1973 | Kaushansky et al. | 250/432 R |

OTHER PUBLICATIONS

"Radiation Sterilization of Pharmaceuticals", *Manufacturing Chemist*, Powell, Nov. 1959, pp. 435–437.
"The Effect of Gamma Radiation on Some Pharmaceutical Products", *JAPA*, Controulis et al., Feb. 1954, pp. 65–69.
"Radiation, Foods New Keeper", *Science News Letter*, Tufty, 01-15-66, pp. 42–43.
"Radiation Preservation of Foods", *Nature*, 12-04-65, pp. 973–974.
"New Horizons in I.V. Feeding", *JAMA*, Feb. 8, 1971, vol. 215, No. 6, pp. 939–949.

*Primary Examiner*—Robert W. Michell
*Assistant Examiner*—Thomas Wallen

[57] ABSTRACT

The disclosure is of a method for preparing a stable, dry-packaged, sterile, nutrient composition which upon addition of sterile, pyrogen-free water is suitable for intravenous administration to a mammal, including a human. The method comprises providing the nutrients in a specific dry form and state of physical purity acceptable for intravenous administration, sealing the nutrients in a particular type of container adapted to receive and dispense sterile fluids and subjecting the container and its sealed contents to a sterilizing, nondestructive dose of ionizing radiation. The method results in a packaged, sterile nutrient composition which may be dissolved by the addition of sterile, pyrogen-free, water. The resulting aqueous intravenous solution may be safely administered to a mammal, including a human, in need of nutrient therapy. The packaged nutrient compositions of the invention exhibit greatly extended storage life and provide an economical method of providing intravenous solutions which are safe and efficacious for use.

20 Claims, 4 Drawing Figures

METHODS OF PREPARING AND USING INTRAVENOUS NUTRIENT COMPOSITIONS

BACKGROUND OF THE INVENTION

1. Field of the Invention

The invention relates to methods of preparing and using nutrient compositions for parenteral administration. More specifically, the invention relates to methods and uses of stable, dry-packaged, sterile, nutrient compositions which upon addition of water are suitable for intravenous administration to mammals.

2. Brief Description of the Prior Art

Prior hereto, commercially available parenteral nutrient compositions were generally prepared in the form of aqueous solutions employing highly sophisticated and costly manufacturing plant facilities. Because of their cost, these facilities are few in number and located long distances from the majority of sites where the solutions are required for use. Accordingly, added costs are generated by the need to transport the aqueous solutions to distant points of use such as hospitals, clinics and like medical facilities.

The need for centralized, costly facilities for preparing parenteral nutrient compositions has been dictated by the need to prepare these compositions ready to use, i.e.; in the form of aqueous solutions meeting the stringent requirements for intravenous administration to a human. This need has been generated over recent years by increasingly stringent standards of sterility, non-pyrogenicity and freedom from extraneous particulate matter, imposed by regulatory health agencies. In fact, the standards now set are of such a high level that as a practical matter they could, heretofore, be achieved economically only at the complex and costly plant facilities referred to above.

There are a number of obvious and not so obvious disadvantages associated with the prior art system for supplying parenteral nutrient compositions at the point of use. Most obvious is the disadvantage of having to store and ship large volumes and weights of water, the major constituent of the parenteral solution. It has been proposed heretofore to prepare the nutrient compositions in a dry-packaged form for shipment to the point of use; see for example U.S. Pat. No. 3,648,697. At the point of use, sterile water is mixed with the dry compositions, to form the solution at the site of use and obviate the storage and shipment of large quantities of water. Unfortunately, the proposal to package and ship dry forms of parenteral compositions has not had commercial success. One of the major reasons for the lack of success has been the inability to produce at the site of use, an aqueous solution of the dry form, which will meet the stringent requirements of sterility, non-pyrogenicity and freedom from particulate matter. This has been due in part to a lack of a method which will provide the dry nutrient composition themselves in a state of acceptable sterility and purity. Even if sterile, pyrogen-free water is available at the site of use for mixing with a dry form of the nutrient composition, the product upon admixture generally has not been satisfactory, failing to meet standards.

By the method of our invention, highly stable, dry-packaged, sterile, pyrogen-free nutrient compositions are provided which upon the addition of sterile, pyrogen-free water will yield solutions of the nutrients meeting the criteria for safe intravenous administration to a human.

In addition, the method of the invention obviates a number of other problems associated with the prior art system of preparing parenteral nutrient solutions, which comprises sterilization by autoclaving. The parenteral solutions are packaged and then subjected to autoclaving to assure sterility. Autoclaving as a method of sterilization permits only certain nutrients to be present in the same solution during sterilization because of the chemical reactivity of these materials under autoclave conditions. For example, amino acids and reducing sugars such as dextrose will combine in a Maillard reaction to form Amadori compounds which are potentially toxic and largely non-utilizable especially when infused intravenously. A further example of the limitation imposed by the prior art method of autoclave sterilization is encountered in regard to vitamins. The autoclave conditions are too severe for many vitamins such as, for example, thiamine, riboflavin, ascorbic acid and the like. These vitamins in particular are rapidly degraded to less than 10 percent of their initial activity when exposed to autoclave conditions and stored in aqueous solution, even for short periods of time.

Further, inherent in autoclave sterilization is a limitation of effectiveness of the method itself. Deaths of patients have been reported and traced to inability to achieve sterile conditions in a number of instances. This is particularly true of the present commercially available solution package, which includes a stopper and a metal cap to secure the stopper to the solution container. It is difficult to achieve sterilizing conditions lethal to bacteria under the metal cap, which is designed to protect the stopper from contamination. It is difficult for sufficient moisture at elevated temperatures to penetrate around the metal cap and sterilize the stopper. Another problem inherent in the use of autoclave as a means of sterilizing is in the use of certain plastic containers for parenteral solutions, wherein autoclave conditions can cause chemical interaction between the plastic formulations and the contained solutions.

By the method of the present invention, many of the problems associated with autoclave sterilization are obviated. For example, many patients require complex solutions containing amino acids, monosaccharides, fats, vitamins, macro-minerals and trace minerals to be administered to them intravenously. Because of the current technology described above, these nutients must be made available to the patient in a plurality of containers. For example, one common method is to provide a bottle of amino acid solution, a bottle of glucose, a bottle of multivitamins and separate bottles with a mineral nutrient in each or a mixture of minerals. A hospital pharmacist or intravenous solution technician then has the responsibility for adding these nutrients together under sterile conditions. This process is laborious and potentially dangerous. Also, it is almost impossible to end up with an exact concentration of final solution because it is difficult to calculate the final solution volume after adding a plurality of nutrient materials. By the method of our invention, heretofore unstable and incompatible drugs and nutrients are conveniently packaged in a single container, in sterile, pyrogen-free condition for ultimate administration to the patient.

The dry-packaged products produced by the method of our invention greatly extend the flexible use of parenteral solutions in nutrient therapy. The method of our invention permits the safe, economic deliverability of simple and complex intravenous solutions at the patient's bedside.

SUMMARY OF THE INVENTION

The invention comprises a method of preparing a stable, dry-packaged, sterile, pyrogen-free, nutrient composition for intravenous administration to a mammal, including a human, which comprises;

Providing the nutrient composition in a solid, form having a moisture content, which is not more than about 30 percent by weight of the solid form, provided that when the nutrient is an amino acid or carbohydrate, the moisture content does not exceed about 15 percent by weight and when the nutrient is a vitamin the moisture content does not exceed about 10 percent by weight, said form being readily dissolved in water at a temperature of circa 185° F. to form an aqueous solution which will pass through a 5 micron filter by gravity at a rate of at least 1 liter per hour and the filtrate thereof will pass through a 0.22 micron filter by gravity at a rate of at least 1 liter per two hours;

sealing the provided nutrient composition in a moisture-proof, microorganism-impermeable, ionizing ray-permeable container adapted to receive and dispense sterile, pyrogen-free fluids; and subjecting the sealed-in compositon to a non-destructive, sterilizing dose of an ionizing ray.

The method of the invention, provides nutrient compositions in a dry-packaged form which may be admixed with sterile, pyrogen-free water suitable for parenteral use to obtain nutrient solution compositions acceptable for infusion into a human being, the compositions being solutions which are totally sterile, pyrogen-free, within acceptable limits of particulate matter and which contain nutrients, and other materials which have not been decomposed or degraded during the process of sterilization.

The invention also comprises the storage stable, dry-packaged articles prepared by the method of the invention and the methods of their use to administer nutrients intravenously to mammals, including humans.

The term "sterile" and "sterilizing" as used throughout the specification and claims is not according to the classical definition formulated by the Council on Pharmacy and Chemistry of the American Medical Association, but rather means the absence (or killing) of undesirable microorganisms within the limits prescribed by the United States Pharmacopia XIX (Page 592) for intravenously administerable fluid compositions.

The term "pyrogen-free" as used herein means a material which will provide a negative reaction in the well-known limulus test for the detection of pyrogens and which meets the requirements of the well-known rabbit test as described in the U.S. Pharmacopia, supra.

The term "ionizing-ray" as used throughout the specification and claims means ionizing radiation. The term "ionizing radiation" means radiation possessing an energy at least sufficient to produce ions or to break chemical bonds and thus includes also radiations such as "ionizing particle radiation" as well as radiations of the type termed "ionizing electromagnetic radiation".

The term "ionizing particle radiation" is used to designate the emission of electrons or highly accelerated, relatively heavy, nuclear particles such as protons, neutrons, alpha particles, deuterons, beta particles, or their analogs directed in such a way that the particle is projected into the mass to be irradiated. Charged particles can be accelerated by the aid of voltage gradient by such devices as accelerators with resonance chambers, Van der Graaff generators, insulating core transformers, betatrons, synchrotrons, cyclotrons and the like. Neutron radiation can be produced by bombarding a selected light metal such as beryllium with positive particles of high energy. Particle radiations can also be obtained by the use of an atomic pile, radioactive isotopes or other natural or synthetic radioactive materials.

"Ionizing electromagnetic radiation" is produced when a metallic target such as tungsten is bombarded with electrons of suitable energy. This energy is conferred to the electrons by potential accelerators over 10,000 electron volts. In addition to radiations of this type, commonly called x-ray, an ionizing electromagnetic radiation suitable for the practice of this invention may be obtained by means of a nuclear reactor (pile) or by the use of natural or synthetic radioactive material, for example, cobalt 60. The use of cobalt 60 as a source of ionizing radiation, producing gamma rays, is preferred in the method of the present invention.

The term "nutrient" is employed in its usually accepted sense as meaning a substance that nourishes; a food material. It includes within its scope sugars, minerals, vitamins, amino acids, protein hydrolyzates, oligopeptides, keto and hydroxy analogues of amino acids, starches and gelatins and the like used for plasma expansion.

The term "drug" is employed in its usually accepted sense as meaning a therapeutic agent and it includes antibiotics, anti-coagulant, anti-arrhythmia drugs, and cancer chemotherapeutic agents and the like.

DETAILED DESCRIPTION OF THE PREFERRED EMBODIMENTS OF THE INVENTION

Figure 1:
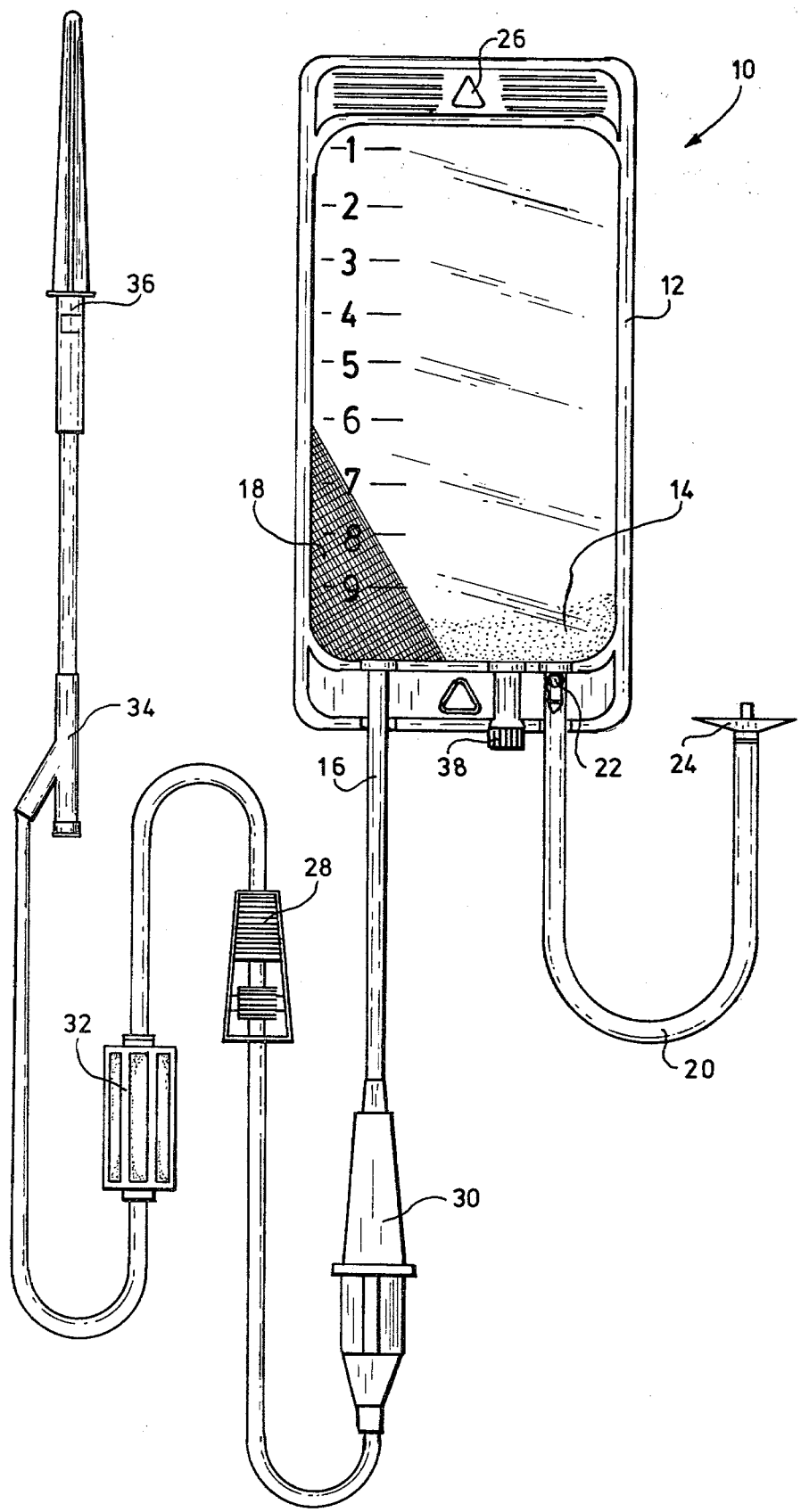
FIG. 1 is a plane view of a packaged nutrient composition prepared according to the method of the invention, together with means for intravenous administration to a mammal.

The nutrient compositions prepared by the method of the invention are represented by amino acids, dextrose, minerals including electrolytes, vitamins, mixtures thereof and like nutrient compositions. They are provided initially in the method of the invention, in solid forms having a purity acceptable, with the exception of sterility, for administration parenterally to a human. They can, of course, be initially provided in a state of sterility acceptable for parenteral administration but that is unnecessary. Essential to the method of the invention is the initial provision of the nutrient compositions having, a minimum moisture content of about 0.2 percent by weight. In the absence of this minimum, sterility may not be achieved in a satisfactory manner, i.e.; the nutrient compositions may be adversely affected or degraded. There are also maximum moisture levels, above which the desired product may not be obtained. The maximum moisture levels will vary however, depending on the specific nutrient composition to be treated in the method of the invention. In general, the maximum allowable moisture content is about 30 percent by weight of the nutrient composition, provided that when the nutrient is an amino acid or carbohydrate the moisture content should not exceed about 15 percent by weight and should preferably be in the range of from about 4 to 8 percent by weight of the composition. When the nutrient is a vitamin, the moisture content should not exceed about 10 percent by weight of the composition and is preferably 3 percent or less. When the nutrient is a mineral the maximum moisture content should not exceed 30 percent by weight. The moisture content should preferably be 20 percent or less. If these maximum moisture contents are exceeded, there is a likelihood that the nutrient would be adversely affected, i.e.; degraded during sterilization.

Advantageously, the provided nutrient composition will be free of pyrogens. This may be assured if the nutrient composition is maintained within the above-described moisture content limits as soon as possible after manufacture, until sterilized by the process of the invention.

It will be appreciated by those skilled in the art that for parenteral administration, it is important that the nutrient compositions employed meet certain standards of purity in regard to particulate matter contaminant. We have found that the product of our method will meet these requirements and standards. Preferably, the initially provided nutrient composition meets the following particulate body test. A production lot of the nutrient composition in dry, solid form is first tumbled in a dry clean container. A randomly selected aliquot is removed and dissolved in a liter of hot (185° F.) water and passed through a 5 micron filter by gravity. The liter sample should pass through the filter within one hour. If the sample does not pass this test, the starting nutrient composition is not preferred for treatment by the method of the invention. The 1 liter solution, if it has passed the initial filter test is then passed through a 0.22 micron filter by gravity. If the filtrate passes through the 0.22 micron filter within a period of 2 hours, it is an indication that the starting nutrient composition is preferred for further processing by the method of the invention. The nutrient material provided for treatment by the method of the invention should also pass the USP XIX test for non-pyrogenicity.

Preferably, the initially provided nutrient compositions will have as low a bioburden as possible, i.e.; they preferably have low bacterial contamination. In the most preferred form, the initially provided nutrient compositions should be free of bacteria to the extent that they will exhibit a plate count of no more than 10 per gram or 1 colony per gram when tested for bacterial presence. If bacterial contamination is kept at a minimum from the time of manufacture of the nutrient composition until processed by the method of the invention, there is a likelihood that the pyrogenicity will be low.

The initially provided nutrient compositions are then hermetically sealed in a moisture-proof, microorganism-impermeable, ionizing ray-permeable container adapted to receive and dispense sterile, pyrogen-free fluids. Preferably, the nutrient compositions are sealed in pouches, multiple containers such as overwraps or similar containers made of non-metallic materials which will effectively exclude infiltration of microorganisms, gas, vapor and moisture over a time period of several years. Such packaging materials are commercially available in numerous forms of polymeric films, including laminates of 2 or more films. For example, the pouches may be constructed of polyethylene, polypropylene, polyethyleneterephthalate, polyvinyl chloride and like polymeric films for forming hermetically sealed pouches. It will be appreciated that the containers should be initially provided in clean, particulate free condition and they may be pre-sterilized to some extent employing conventional techniques such as ultra-violet radiation and the like.

After the nutrient compositions are sealed in the above-described containers, they are subjected, according to the method of the invention, to a non-destructive (non-degrading), sterilizing dose of an ionizing ray as defined above.

We have found that a non-degrading sterilizing dose of ionizing radiation for the sealed in nutrient compositions is advantageously within the range of from about 0.5 to 6.0 megarads; preferably not more than 4.0. Radiation within this dosage range may be carried out at room temperature or below or at elevated temperatures if so desired. The temperature at which radiation is carried out is not critical to the method of the invention. However, practical temperatures are within the range of from about minus 10° to about 50° C. Lower radiation dosages will not be effective in sterilizing the sealed in nutrient compositions. Higher doses will generally degrade (destroy) either the package container or the nutrient composition contained therein or both. This of course is undesirable. For this reason, preferably the dosage employed for sterilizing the sealed in nutrient compositions is within the range of from about 1 to about 3 megarads, most preferably circa 2.5 megarads.

It is possible, however, to employ higher doses of radiation without degrading the packages or nutrient compositions under certain conditions. For example, this may be accomplished by first lowering the sealed in nutrient compositions to extremely low temperatures, i.e.; at or about the temperature of liquid nitrogen (−195.8° C. to −209.9° C.). Cooling of the nutrient compositions and their containers to these low temperatures prior to irradiation may also speed sterilization. In addition, if the nutrient compositions are exceptionally dry, for example having a moisture content of less than one percent by weight, radiation doses of up to 6 megarads will not detectably degrade the nutrient compositions.

It may be observed from the above-discussion that the dosage of ionizing rays may be varied to some extent particularly depending on the moisture level of the material for irradiation. The lower the moisture level, the higher will be toleration to sterilizing doses without degradation of the nutrient material.

Irradiation as described about may also be carried out advantageously in the absence of oxidizing agents, i.e.; in an atmosphere having an oxygen concentration which is reduced to such a degree that the quantity of oxygen molecules present is sufficient to react during irradiation with the nutrient compositions and their packaging materials. The reduction of the oxygen presence can be obtained by packaging the nutrient compositions under and in the presence of an inert gaseous atmosphere such as nitrogen or by the use of partial vacuum packing. The irradiation in the presence of nitrogen rather an oxygen atmosphere reduces the secondary or "indirect" destructive effects of radicals generated in the presence of water or oxygen. There is only a "direct" effect of direct bombardment by the ionizing rays.

As mentioned above, gamma radiation produced by cobalt 60 is a preferred ionizing ray for employment in the method of the invention. Gamma radiation produced by cobalt 60 has a high penetrating ability and obviates the need for concern about the thickness of the nutrient composition to be penetrated.

It is well-known that microorganisms exposed to radiation, including gamma radiation, do not always die immediately. In some bacteria, which have been subjected to a radiation dose which prevents their multiplication, many biological functions continue for extended periods of time. For this reason, sterility testing to be carried out as a control mechanism for the method of the invention should be delayed for a period of about four days following radiation.

Apparatus for producing ionizing rays and techniques of their application to a wide variety of materials, including for example foodstuffs, are so well-known that further description need not be given herein. Those skilled in the art will appreciate the techniques of ionizing ray application.

Referring now to FIG. 1, a plane view of a dry-packaged, nutrient composition prepared according to the method of the invention, one will gain a greater appreciation of the preferred embodiments of the invention. As shown in FIG. 1, a dry-package 10 is shown which comprises a polymeric film, hermetically sealed pouch 12 containing a nutrient composition such as, for example, dextrose powder 14. The pouch 12 also contains at one end between dextrose powder 14 and an outlet conduit 16 a 10 micron particulate screen 18. An inlet conduit 20 communicates with the interior of the pouch 12 when ball valve 22 is open. The pouch 12 with its contained dextrose powder 14 was hermetically sealed under vacuum conditions and irradiated with gamma radiation according to the above described method of the invention. When the nutrient composition is desired for administration intravenously to a patient requiring nutritional therapy, sterile, pyrogen-free, water is introduced through the conduit 20, passed valve 22 via a sterile connector 24 device which may be attached to a source of sterile, pyrogen-free, water. After the sterile, pyrogen-free, water is introduced into the interior of pouch 12, ball valve 22 closes and the dextrose powder 14 may be dissolved by kneading or gently shaking the pouch 12. Indicia may be printed on the surface of pouch 12 as shown in FIG. 1, to provide an indication of volume of water introduced into the pouch 12. To administer the dissolved dextrose powder 14 to a patient, the pouch 12 may be hung up through the aperture 26 and roller clamp 28 opened to permit flow of the solution from the interior of pouch 12 through screen 18 and into the conduit 16. Conduit 16 may be interrupted with a drip chamber 30 and additional in-line filters such as a 0.22 micron filter 32. The conduit 16 may also include a "Y" type of medication injection port 34. An adapter and needle 36 may be fitted to the open end of conduit 16 and upon insertion of the needle 36 into a mammalian vein, the solution of dextrose is dispensed therein, controlled by clamp 28. Additional means in the form of an injection port 38 may be provided for mixing medications with the dissolved dextrose powder 14. In a preferred package of the invention, the entire pouch 12 with its preassembled conduit 16, adapter and needle 36 and other components as described above are provided in a single, hermetically sealed, bacteria-impermeable outer package wherein all parts have been sterilized by ionizing radiation as described above. For use, the operator need only open the outer sterile package, remove the pouch 12 with its attached ancillary components, transfer sterile, pyrogen-free water to the interior of pouch 12 using sterile technique, affect the solution of the dextrose powder 14, make an intravenous entry of the patient with needle 36 and administer the dissolved nutrient solution employing sterile technique and conventional procedure.

It will be appreciated from the above, that one can provide a storage-stable, dry-packaged parenteral composition at a point or place, remote from the manufacturing facility. Immediately before use, the parenteral water is added to finally prepare a solution. Portable apparatus is available to provide the sterile, pyrogen-free water for the preparation of the final solution; see for example U.S. Pat. No. 4,089,749.

In relation to FIG. 1, a single nutrient composition, dextrose, was described in pouch 12 for illustrative purposes. It will be appreciated, that it may be desired to provide mixture of nutrient compositions for administration to the mammal suffering from a nutritional deficiency. Generally, it is desired that the different classes of nutritional compositions be maintained separate from each other until dissolution in aqueous medium is desired. For example, as mentioned previously, amino acids and dextrose mixed together for any significant period of time will produce Maillard reactions even at moderate moisture levels and room temperature. This ultimately shortens the shelf life for the packaged, mixed nutritional composition. Also, it will be appreciated from the previous discussion that some nutritional compositions must be maintained at moisture contents differing from contents for other nutritional compositions. For example, minerals are generally very hygroscopic, drawing under normal ambient conditions as much as 20 to 30 percent moisture. Several salts are also hydrates, which would tend to bring water into the interior of the hermetically sealed container. Desirably, such minerals are segregated from the normally drier amino acids and/or dextrose materials.

Figure 2:
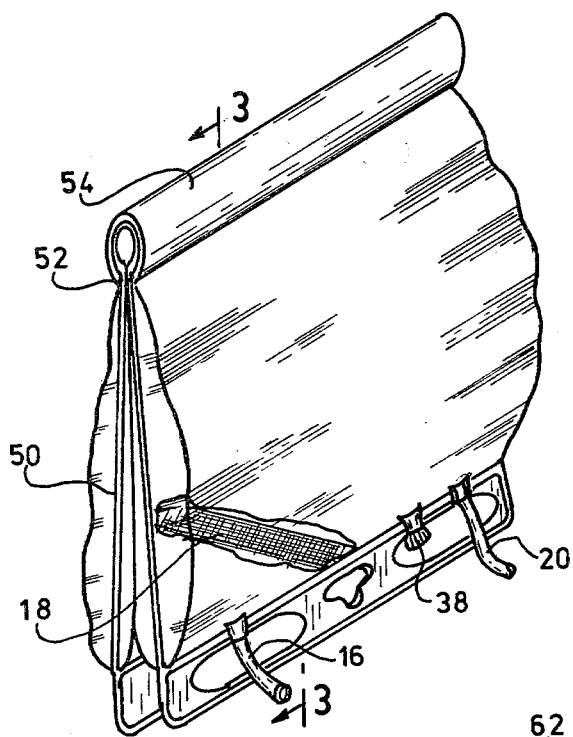
FIG. 2 is an isometric view of another embodiment packaged nutrient form of the invention.
Figure 3:
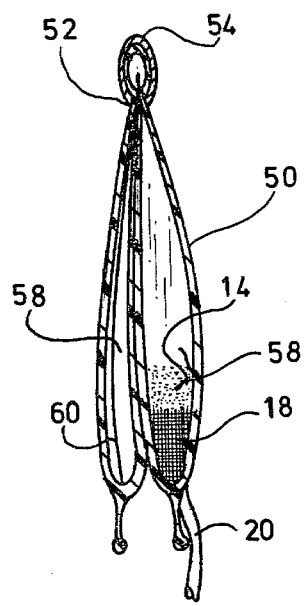
FIG. 3 is a cross-sectional view along lines 3—3 of FIG. 2.

Referring now to FIG. 2, another embodiment package is shown, for the packaging of a plurality of dry nutritional compositions in a single unit, storage stable until it is desired to form a solution and immediately administer the solution to a human requiring such therapy. As shown in FIG. 2 the pouch 50 comprises a polymeric film pouch quite similar to the pouch 12 previously described. The pouch 50 however is folded once at its mid-section to form a fold line 52 and secured with a "U" member 54. This effectively provides the interior chamber formed by pouch 50 with two separate chambers. Construction details of the pouch 50 may be observed by viewing FIG. 3, a cross-sectional view along lines 3—3 of FIG. 2. Thus, it is seen that the fold secures pouch 50 to provide the two interior chambers 56, 58 and the fold is secured by the dividing clamp member 54.

Figure 4:
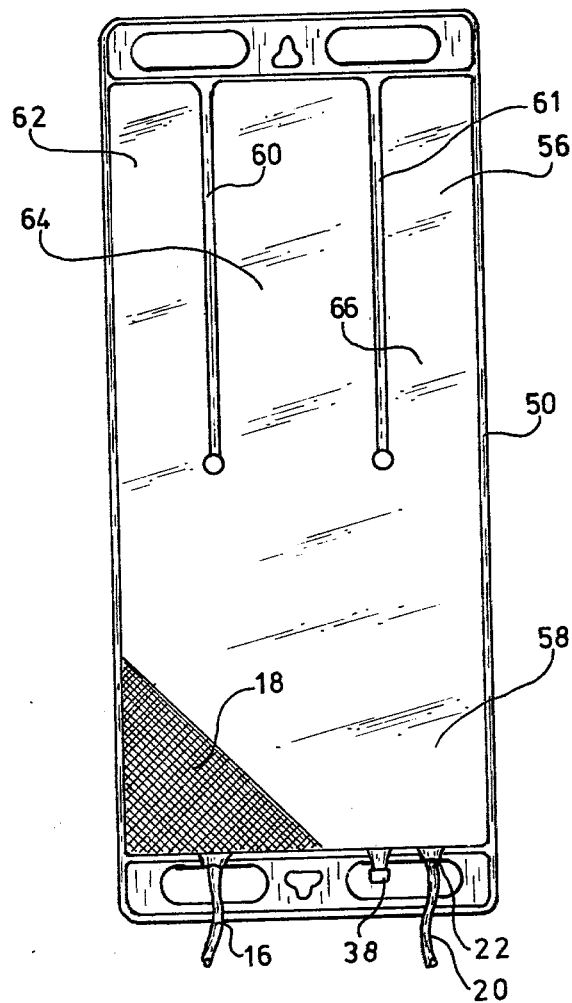
FIG. 4 is a partial view of the embodiment package seen in FIG. 3, but unfolded.

Referring now to FIG. 4, one may see an isometric view-in-part of the pouch 50 as shown in FIG. 2 but with the clamp member 54 removed and the pouch 50 in an open condition. In this condition, the chambers 56, 58 are in open communication with one another. As also shown in FIG. 4, by heat sealing of the pouch sides, walls 60 and 61 are formed in the chamber 56 to form segregated sub-chambers 62, 64 and 66 within the chamber 56. Within the smaller chambers 62, 64 and 66 one may emplace and segregate minerals, amino acids, drugs and/or vitamins from each other within the chamber 56. In the chamber 58 one may then place for example a carbohydrate such as dextrose. It will be readily observed that under these conditions, a single pouch 50 may be employed to effectively contain and yet segregate from each other minerals, amino acids, vitamins and carbohydrates prior to the time when it is wished to admix them in an aqueous solution. In other respects, the pouch 50 is similar to the package of embodiment 10 shown in FIG. 1 in that there is integrally attached thereto a conduit 16, with drip chamber 30, filter 32, injection port 34, adapter and needle 36, clamp 28, conduit 20, valve 22 and sterile connection 24, all of which function as described in relation to package 10 (not all of which are shown in FIG. 4). In operation, one merely removes the clamping member 54 and inserts sterile, pyrogen-free, particulate-free water as described in relation to the package 10. Administration to a human is also as described for the package 10.

The following examples describe the manner and process of making and using the invention and set forth the best mode contemplated by the inventors of carrying out the invention but are not to be construed as limiting. In carrying out the examples the following tests, where reported, were used:

Pyrogen—representative samples are subjected to a limulus test for chemical detection of pyrogen. If positive for pyrogen by limulus, the lot is rejected. If the sample is not positive or is slightly positive for pyrogen, the sample is further tested by the rabbit test as outlined in U.S. Pharmacopia, XIX. If the temperatures are zero or are elevated, but under 1° C. for each of the three rabbits, the sample is accepted and passed for further processing. If the sum of temperatures in the three rabbits is higher than 3° C., the lot is rejected.

Sterility—representative samples if irradiated materials are tested by standard techniques for total plate count. Those samples that are found to be negative are then serially diluted on slant tubes in accordance with the techniques recommended in U.S. Pharmacopia, XIX, for sterility.

Amino acid integrity. Controls (pure samples) are compared with treated (irradiated) samples on a standard liquid chromatography amino acid analyzer. Dextrose integrity. Dextrose (pure samples) are compared with treated (irradiated) samples by means of optical rotation for gross differences and silyl ester derivatives are examined by gas-liquid chromatography for degradation products.

EXAMPLE 1

A flexible, polyvinyl chloride pouch type container having a capacity of 500 milliliters is selected, which has been cleaned of particulate matter by washing and clean air blowing. Several of the pouches are each charged with 25 grams of anhydrous dextrose powder having a moisture content of 8.8 percent (Karl Fischer method) and a bacteria count of less than 10 per gram. The dextrose powder was selected from a production lot which was tested for particulate matter by dissolving 250 grams of the dextrose in 1,000 milliliters of hot water (185° F.) and passing the solution through a 5 micron particulate filter in less than 1 hour and passing the filtrate through a 0.22 micron air and bacteria filter by gravity in less than 2 hours. Upon testing for pyrogens as described above, the lot is found to be pyrogen-free. The containers with contents of anhydrous dextrose powder are purged with nitrogen gas and sealed under vacuum, hermetically. The filled containers are then subjected to a cobalt 60 source until they receive a variety of radiation doses. After 4 days, the sealed, irradiated package is charged with 500 milliliters of sterile, pyrogen-free water to make a 5 percent aqueous dextrose solution. Aliquots of the solution are subjected to tests for sterility, particulate matter, degradation of nutrient composition and pyrogens. The radiation doses employed and the test results are shown in Table 1, below

TABLE 1

| Package No. | Radiation Dose (Megarads) | Meets USP XIX Standards for Sterility, Non-Pyrogenicity | Nutrient Integrity | |
|---|---|---|---|---|
| | | | % Glucose By Optical Rotation | % Glucose By Gas Chromatography |
| 9 | 0.62 | — | 99.7 | 74 |
| 10 | 1.25 | — | 100.6 | 96 |
| 11 | 2.50 | — | 99.6 | 97 |
| 12 | 0.62 | Yes | — | |
| 13 | 1.25 | Yes | — | |
| 14 | 2.50 | Yes | — | |
| 15 (Control) | None | | 99.9 | 99 |
| 16 (Control) | None | Possible Pyrogen | | |

Packages 12, 14 and 16 were tested for presence of particulate matter as described above and found to be free of particulate matter.

EXAMPLE 2

The procedure of Example 1, supra., was repeated except that the dextrose powder had a moisture content of 0.4 percent. The test results are shown in Table 2, below.

TABLE 2

| Package No. | Radiation Dose (Megarads) | Meets USP XIX Standards for Sterility, and Non-Pyrogenicity | Nutrient Integrity (% Glucose) By Gas Chromatography |
|---|---|---|---|
| 33 | 0.62 | — | 104 |
| 34 | 1.25 | — | 105 |
| 35 | 2.50 | — | 100 |
| 36 | 0.62 | Yes | — |
| 37 | 1.25 | Yes | — |
| 38 | 2.50 | Yes | — |
| 40 (Control) | None | No | — |

EXAMPLE 3

The procedure of Example 1, supra., was repeated except that the anhydrous dextrose as used therein was replaced with a mixture of the following minerals:

| Minerals | Milliequivalents |
|---|---|
| Sodium chloride | 45 |
| Potassium acetate | 25 |
| Potassium acid phosphate | 12 |
| Magnesium sulfate | 2 |
| Calcium gluconate | 1 |
| Zinc sulfate | 5 |
| Copper sulfate | 1 |

The mixture of minerals had a moisture content of 15.8 percent. 15 grams of the mineral composition was sealed in the pouch container as described in Example 1 and irradiated. The levels of irradiation and the test results are shown in Table 3, below.

TABLE 3

| Package No. | Radiation Dose (Megarads) | Meets USP XIX Standards For Sterility and Non-Pyrogenicity |
| --- | --- | --- |
| 41 | 0.62 | Yes |
| 42 | 1.25 | Yes |
| 43 | 2.50 | Yes |
| 44 | 0.62 | Yes |
| 45 | 1.25 | Yes |
| 46 | 2.50 | Yes |
| 48 (Control) | None | No |

EXAMPLE 4

Following the procedure of Example 1, supra., but replacing the anhydrous dextrose as used therein with 2.5 grams of a vitamin mixture consisting of:

| Vitamins | Proportion |
| --- | --- |
| Ascorbic acid | 500 milligrams |
| Thiamine hydrochloride | 25 milligrams |
| Riboflavin | 5 milligrams |
| Pyridoxine hydrochloride | 7.5 milligrams |
| Niacinamide | 50 milligrams | having a moisture content of less than 20 percent, there is obtained a vitamin solution which upon testing is shown to be sterile and free of pyrogens.

EXAMPLE 5

Repeating the procedure of Example 1, supra., but replacing the anhydrous dextrose as used therein with 42.5 grams of the following amino acid mixture:

| Amino Acids | Parts |
| --- | --- |
| L-isoleucine | 5.9 |
| L-leucine | 7.7 |
| L-lysine acetate | 8.7 |
| L-methionine | 4.5 |
| L-phenylalanine | 4.8 |
| L-threonine | 3.4 |
| L-tryptophan | 1.3 |
| L-valine | 5.6 |
| L-alanine | 6.6 |
| L-arginine | 3.1 |
| L-histidine | 2.4 |
| L-proline | 9.5 |
| L-serine | 5.0 |
| glycine | 17.0 |

L-cysteine hydrochloride hydrate less than 0.02 having a moisture content of 7.9%, there is obtained an intravenous solution of the amino acids. The test results are shown in Table 4, below.

TABLE 4

| Package No. | Radiation Dose (Megarads) | Meets USP XIX Standards for Sterility and Non-Pyrogenicity | Amino Acid Integrity |
| --- | --- | --- | --- |
| 1 | 0.62 | — | No Degradation |
| 2 | 1.25 | — | No Degradation |
| 3 | 2.50 | — | No Degradation |
| 4 | 0.62 | Yes | — |
| 5 | 1.25 | Yes | — |
| 6 | 2.50 | Yes | — |
| 7 (Control) | 0 | — | No Degradation |
| 8 (Control) | 0 | No | — |

Packages 4, 6 and 8 were tested for particulate matter and found to be free of such matter.

Those skilled in the art will appreciate that many modifications may be made to the above-described preferred embodiments without departing from the spirit and scope of the examination. For example, drugs and like medications may be included with the nutrient compositions prepared by the method of the invention, admixed therewith if compatible or segregated in a separate pouch of the container of FIG. 2 if it is desired to maintain separate until use. Representative of such drugs are antibiotics, antifungals and the like.

What is claimed:

1. A method of preparing a stable, dry-packaged, sterile, pyrogen-free nutrient composition for intravenous administration to a mammal, which comprises;

providing the nutrient composition in a solid form having a moisture content, which is not less than about 0.2 and not more than about 30 percent by weight of the solid form, provided that when the nutrient is an amino acid or carbohydrate, the moisture content does not exceed about 15 percent by weight and when the nutrient is a vitamin the moisture content does not exceed about 10 percent by weight, said form being readily dissolved in water at a temperature of circa 185° F. to form an aqueous solution which will pass through a 5 micron filter by gravity at a rate of at least 1 liter per hour and the filtrate will pass through a 0.22 micron filter by gravity at a rate of at least 1 liter per 2 hours;

sealing the provided nutrient composition in a moisture-proof, microorganism-impermeable, ionizing ray-permeable container adapted to receive and dispense sterile, pyrogen-free fluids; and subjecting the sealed-in nutrient composition to a non-destructive, sterilizing dose of an ionizing ray.

2. The method of claim 1 wherein the nutrient composition is cooled to a temperature of liquid nitrogen (−195.8° C. to −209.9° C.) prior to the step of subjecting.

3. The method of claim 1 wherein said nutrient composition comprises an amino acid.

4. The method of claim 1 wherein said nutrient composition comprises dextrose.

5. The method of claim 1 wherein said nutrient composition comprises a vitamin.

6. The method of claim 1 wherein said nutrient composition comprises a mineral.

7. The method of claim 1 wherein the container is a pouch formed from a polymeric film.

8. The method of claim 1 wherein said ionizing ray is a gamma ray.

9. The method of claim 8 wherein the sterilizing dose is within the range of from 0.5 to 6.0 megarads.

10. The method of claim 1 wherein there are a plurality of different nutrient compositions sealed in said container.

11. A dry-packaged article of manufacture for the containment and intravenous administration of a sterile, pyrogen-free, particulate-free nutrient composition to a mammal, which comprises;

a hermetically sealed, moisture-proof microorganism-impermeable, ionizing ray permeable container adapted to contain the composition in dry form and aqueous mixture;

a nutrient composition in a solid form having a moisture content which is not more than about 30 percent by weight of the solid form, provided that when the nutrient is an amino acid or carbohydrate, the moisture content does not exceed about 15 percent by weight and when the nutrient is a vitamin the moisture content does not exceed about 10 percent by weight, said form being readily dissolved in water at a temperature of circa 185° F. to form an aqueous solution which will pass through a 5 micron filter by gravity at a rate of at least 1 liter per hour and the filtrate will pass through a 0.22 micron filter by gravity at a rate of at least 1 liter per 2 hours, disposed within said container;

means for introducing into the container sterile, pyrogen-free water in a proportion sufficient to form an intravenous mixture of the water and said nutrient composition in the container, connected to the container;

means connected to the container, for administering the intravenous mixture to a mammal;

filter means associated with the means for administering, adapted to remove particulate matter from the intravenous mixture; and a bacteria-impermeable covering hermetically enclosing the container and the connected and associated means;

said enclosed container and means being sterile and the nutrient composition being sterile and pyrogen-free, sterility being achieved by ionizing ray.

12. The article of claim 11 wherein said container has flexible walls.

13. The article of claim 11 wherein said container is divided internally into a plurality of chambers, each chamber adapted to contain a different composition separate from each other in dry form but in admixture in aqueous mixture, said plurality of chambers being openable to each other.

14. The article of claim 11 wherein said composition comprises an amino acid.

15. The article of claim 11 wherein said composition comprises a carbohydrate.

16. The article of claim 11 wherein said composition comprises a vitamin.

17. The article of claim 11 wherein said composition comprises a mineral.

18. The article of claim 11 wherein said means for introducing comprises a conduit having a first end opening inside said container, a second end outside of the container adapted to connect to a source of sterile, pyrogen-free water and valve means for opening and closing said conduit.

19. The article of claim 11 wherein said means for administering comprises a conduit having a first end opening inside the container and a second end opening outside the container, said second end being adapted to make a venepuncture.

20. The article of claim 11 wherein said filter means is a 0.22 micron filter.

* * * * *

UNITED STATES PATENT AND TRADEMARK OFFICE
CERTIFICATE OF CORRECTION

PATENT NO. : 4,282,863
DATED : August 11, 1981
INVENTOR(S) : Myron A. Beigler and Amin J. Khoury It is certified that error appears in the above—identified patent and that said Letters Patent is hereby corrected as shown below:

On the Title page Item [73] insert Assignee --Delmed, Inc., Newton, Massachusetts --

Col. 2, line 48; - "nutients" should read -- nutrients --

Col. 2, line 62; - "imcompatible" should read -- incompatible --

Signed and Sealed this

Twenty-third Day of March 1982

[SEAL]

Attest:

GERALD J. MOSSINGHOFF

Attesting Officer    Commissioner of Patents and Trademarks